US006441252B1

(12) United States Patent
Levin et al.

(10) Patent No.: US 6,441,252 B1
(45) Date of Patent: Aug. 27, 2002

(54) APPARATUS FOR PRODUCING PHENOL USING REACTIVE DISTILLATION

(75) Inventors: Doron Levin, Bala Cynwyd; Jose G. Santiesteban, West Chester, both of PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/991,831

(22) Filed: Nov. 14, 2001

Related U.S. Application Data

(62) Division of application No. 09/468,465, filed on Dec. 21, 1999.

(51) Int. Cl.[7] ............................ C07C 37/08; B01J 8/06
(52) U.S. Cl. ................... 568/798; 568/385; 568/485; 568/741; 568/754; 203/50; 203/57; 203/DIG. 6; 422/211; 422/312
(58) Field of Search .................. 568/798, 385, 568/485, 741, 754; 203/50, 57, DIG. 6; 422/211, 312

(56) References Cited

U.S. PATENT DOCUMENTS

| | | | | | |
|---|---|---|---|---|---|
| 4,870,217 A | * | 9/1989 | Knifton | ....................... | 568/798 |
| 4,935,577 A | * | 6/1990 | Huss et al. | ................... | 585/726 |
| 5,055,627 A | * | 10/1991 | Smith et al. | ................. | 585/467 |
| 5,463,136 A | | 10/1995 | Blackbourn et al. | ........ | 568/385 |
| 5,518,699 A | * | 5/1996 | Kashnitz et al. | ............. | 422/211 |
| 5,705,711 A | * | 1/1998 | Preston | ........................ | 568/697 |
| 5,905,178 A | * | 5/1999 | Hildreth | ...................... | 585/258 |

FOREIGN PATENT DOCUMENTS

EP        0018159        10/1980

\* cited by examiner

*Primary Examiner*—S Padmanabhan
(74) *Attorney, Agent, or Firm*—Darryl M. Tyus

(57) ABSTRACT

An apparatus for producing phenol and acetone from cumene hydroperoxide comprises a reactive distillation column comprising at its upper portion a distillation column and at its lower portion a catalyst bed.

6 Claims, 2 Drawing Sheets

APPARATUS FOR PRODUCING PHENOL USING REACTIVE DISTILLATION

This application is a divisional of U.S. Ser. No. 09/468,465 filed Dec. 21, 1999.

BACKGROUND OF THE INVENTION

1. Field of the Invention

This invention relates to the production of phenol and more particularly to a process for producing phenol and acetone from cumene hydroperoxide (CHP) using reactive distillation.

2. Description of the Prior Art

Phenol is an important organic chemical with a wide variety of industrial uses. It is used, for example, in the production of phenolic resins, bisphenol-A and caprolactam. A number of processes are currently in use for the production of phenol but the single process providing the largest proportion of the total production capacity is the cumene process which now accounts for over three quarters of the total U.S. production. The basic reaction involved in this process is the cleavage of cumene hydroperoxide into phenol and acetone:

The reaction takes place under acid conditions with the yield of both phenol and acetone generally being 40 percent or more.

On an industrial scale, the cumene hydroperoxide is usually treated with dilute sulphuric acid (0.5 to 25 percent concentration) at a temperature of about 50° to 70° C. After the cleavage is complete, the reaction mixture is separated and the oil layer distilled to obtain the phenol and acetone together with cumene, alpha-methylstyrene, acetophenone and tars. The cumene may be recycled for conversion to the hydroperoxide and subsequent cleavage. The phenol produced in this way is suitable for use in resins although further purification is required for a pharmaceutical grade product.

The heterogeneous cleavage of cumene hydroperoxide (CHP) over various solid acid catalysts has already been reported. For example, U.S. Pat. No. 4,490,565 discloses the use of zeolite beta in the cleavage of cumene hydroperoxide, whereas U.S. Pat. No. 4,490,566 discloses the use of a Constraint Index 1–12 zeolite, such as ZSM-5, and EP-A-492807 discloses the use of faujasite in the same process. The use of smectite clays in the acid-catalyzed decomposition of cumene hydroperoxide is described in U.S. Pat. No. 4,870,217.

U.S. Pat. No. 4,898,995 discloses a process for the coproduction of phenol and acetone by reacting cumene hydroperoxide over a heterogeneous catalyst consisting of either an ion exchange resin having sulfonic acid functionality or a heteropoly acid, such as 12-tungstophosphoric acid, on an inert support, such as silica, alumina, titania and zirconia. Such heteropoly acid catalysts are generally used as their hydrates, and as such are inherently unstable at temperatures in excess of 350° C.

Catalytic distillation has been used to produce cumene by alkylating propylene with benzene. See, J. Shoemaker, et al., Cumene by Catalytic Distillation, Hydrocarbon Processing, p. 57, (June, 1987).

U.S. Pat. No. 4,935,577 to Huss, Jr., et al. discloses the use of Lewis acid promoted inorganic oxide catalyst systems for alkylation and oligomerization processes using catalytic distillation.

U.S. Pat. No. 5,055,627 to Smith, Jr., et al. discloses an alkylation process for preparing cumene from benzene and propylene in a zeolitic catalyst bed disposed in a distillation column reactor. The alkylated benzene is withdrawn from the distillation column reactor at a point below the fixed bed and unreacted organic aromatic compound may be taken off as an overhead.

U.S. Pat. No. 5,905,178 to Hildreth discloses a process for removing alpha-methyl styrene from admixtures with cumene by hydrogenation using catalytic distillation to selectively hydrogenate the side chains and produce cumene. The alpha-methyl styrene is produced as a byproduct in the cumene-phenol peroxidation process.

It is an object of the present invention to provide a process for the production of phenol and acetone using catalytic distillation. This process would provide a method of reacting cumene hydroperoxide which would avoid excessive heat buildup and utilize cumene hydroperoxide's high heat of reaction (60.6 kcal/mol) to separate out low boiling point decomposition products, such as acetone.

SUMMARY OF THE INVENTION

The present invention relates to a process for producing phenol and acetone from cumene hydroperoxide, wherein the process comprises the steps of:

i) introducing a cumene hydroperoxide feed into a reactive distillation column comprising at its upper portion a distillation column and at its lower portion a catalyst bed, at a point above or at an upper portion of said catalyst bed;

ii) mixing a diluting portion of acetone with said cumene hydroperoxide to provide a diluted cumene hydroperoxide;

iii) directing said diluted cumene hydroperoxide through said catalyst bed under conditions sufficient to effect the exothermic decomposition of said cumene hydroperoxide to a product comprising a heavy fraction comprising and a vaporized light fraction comprising acetone;

iv) withdrawing said heavy fraction as bottoms from said column;

v) flowing said vaporized light fraction upwards through the catalyst bed and at least a portion of the reactive distillation column;

vi) condensing said light fraction to provide at least a portion of said diluting portion of acetone for subsequent mixing with said cumene hydroperoxide feed;

vii) optionally withdrawing a portion of said light fraction as overhead from said column; and viii) repeating steps i) through vii).

Steps v) and vi) can be used to control dilution of the cumene hydroperoxide feed, e.g., by setting the reflux rate of acetone through said column. The liquid flow of the diluted cumene hydroperoxide through the reactor is preferably maintained at a rate sufficient to keep the catalyst bed wetted, thereby maintaining catalyst temperature at or near the boiling point of the liquid to provide isothermal operation of the process. Given that step vii) is optional, the presently claimed process includes operation under conditions of total reflux with all overhead product being returned to the column.

The diluting portion of acetone can be added to at least one of: 1) the upper portion of the distillation column, 2) the lower portion of the distillation column, upstream of said catalyst bed, e.g., at the CHP feed tray, and 3) the cumene hydroperoxide feed prior to its introduction to said distillation column. Recovered overhead which contains acetone can also be added directly at one or more locations to the catalyst bed in amounts sufficient to reduce formation of heavy compounds, i.e., compounds with normal boiling points greater than 182° C., e.g., dimers of α-methylstyrene (AMS). Such interstage injection of acetone diluent can be used to assist in maintaining the catalyst bed at a temperature at or near the boiling point of the reactant liquid to provide preferred isothermal operation, while eliminating reactor "hot spots."

In another aspect, the present invention relates to an apparatus for preparing phenol from cumene hydroperoxide which comprises:

a) a reactive distillation column comprising at its upper portion a distillation column and its lower portion a catalyst bed;

b) a lower outlet downstream of the catalyst bed for removing high boiling bottom products comprising phenol;

c) an inlet at or near the bottom of said distillation column for introducing cumene hydroperoxide feed at a point upstream of said catalyst bed;

d) an upper outlet for removing low boiling overhead products comprising acetone;

e) a heat exchanger upstream of said upper outlet for cooling said overhead products;

f) an overhead products receiver upstream of said heat exchanger having an outlet from which said overhead products are collected and/or returned to said distillation column; and g) overhead products inlet at an upper portion of said distillation column for introducing overhead products reflux from said receiver.

The apparatus can further comprise an element selected from the group consisting of h) an overhead products inlet at a lower portion of said distillation column for introducing overhead products from said receiver to said distillation column at or near said inlet for introducing cumene hydroperoxide;

i) an overhead products line which recycles overhead products to the cumene hydroperoxide feed upstream of said inlet for introducing cumene hydroperoxide; and j) an overhead products line which recycles overhead products to one or more portions of the catalyst bed.

The process and apparatus of the invention can achieve at or near 100% conversion of cumene hydroperoxide at long on-stream times with high selectivity to phenol and acetone and with extremely low coproduction of high boiling impurities such as 4-cumylphenol, and 2,4-diphenyl-4-methyl-1-pentene. Moreover, the present invention allows efficient use of the heat of reaction evolved from decomposition of cumene hydroperoxide to effect separation of lower boiling products, e.g, acetone, from the reaction product mixture. Such an arrangement minimizes reboiler use, reducing energy costs, while providing higher yields, good product purity and lower capital investment.

DESCRIPTION OF SPECIFIC EMBODIMENTS

Figure 1:
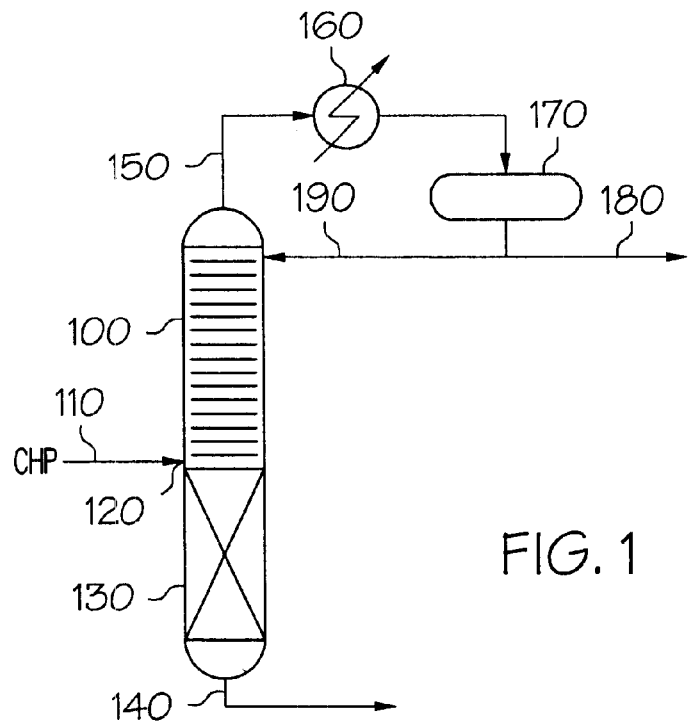
FIG. 1 depicts a flow diagram for an embodiment of the present invention wherein reflux acetone is introduced at the top of the distillation column.

In catalytic distillation a reaction zone containing catalyst is fitted into a fractionation tower equipped with an overhead condenser, reflux pump, reboiler, overhead receiver and control instrumentation. Feed components are introduced above the catalyst bed. Products are continuously removed from the reaction zone by the distillation process.

Catalytic distillation is suitable only for chemical reactions where the distillation of reaction components occurs in the same temperature range as the reaction. Thus, operation above the critical point can be a limitation, and the presence of azeotropes or close boiling components may cause difficulties.

Inasmuch as distillation columns are typically operated at higher liquid and vapor flow rates than conventional reactors, the reduced residence time in the reactive section of the column of the present invention will minimize the formation of byproducts. This is especially advantageous in the case of CHP decomposition as the dehydration of 2-phenyl-2-propanol leads to the formation of α-methylstyrene (AMS), a reactive intermediate that could undergo further reactions such as dimerization, oligomerization, and coke formation. Minimizing the formation of heavy compounds will extend catalyst life if a heterogeneous catalyst is employed for the reactive section of the column.

The preferred conditions for the decomposition reaction include temperature and pressure ranges that are suitable for use in a distillation column. Due to the high heat of reaction, decomposition preferably takes place under dilute CHP concentrations, of the order of less than 50 wt. %, preferably 0.1 to 25 wt. %, and most preferably 0.5 to 5 wt. %, e.g., about 3 wt. % CHP. The feed to the tower can range from 25 to 95 wt. %, preferably 75 to 85 wt. %, e.g., 80 wt. % CHP, and needs to be further diluted, preferably by acetone, to the above-noted levels. Control of the dilution level can be achieved by setting the reflux rate through the tower, or directly adding the recycled overhead containing acetone to the cumene hydroperoxide feed.

Table 1 lists the normal boiling points for the major components involved in the decomposition of cumene hydroperoxide. Acetone has a significantly lower boiling point than all the other major components, thereby facilitating its separation in a reactive distillation column. Other low boiling components may also be present in the column, e.g., methanol, acetaldehyde, and benzene.

TABLE 1

| Component | Normal Boiling Point (° C.) |
| --- | --- |
| Acetone | 56.3 |
| Cumene | 152.4 |
| α-Methylstyrene | 165.5 |
| Phenol | 181.8 |
| 2-Phenyl-2-Propanol | 192.6 |
| Acetophenone | 202.0 |

The catalyst employed can be either a homogeneous or heterogeneous catalyst. Suitable homogeneous catalyst systems can employ a suitable catalyst such as dilute (0.01 to 5 percent concentration) sulfuric acid. Other acids such as perchloric acid, phosphoric acid, p-toluenesulfonic acid, and sulfur dioxide are also effective homogeneous catalysts.

Suitable heterogeneous catalysts for use in the cleavage of cumene hydroperoxide include solid acid catalysts such as zeolite beta, disclosed in U.S. Pat. No. 4,490,565; a Constraint Index 1–12 zeolite, such as ZSM-5, disclosed in U.S. Pat. No. 4,490,566; faujasite, disclosed in EP-A-492807; smectite clays, described in U.S. Pat. No. 4,870,217; ion exchange resins having sulfonic acid functionality or heteropoly acids, such as 12-tungstophosphoric acid, on an inert support, such as silica, alumina, titania and zirconia, disclosed in U.S. Pat. No. 4,898,995. Additional solid-acid catalysts suited for use in the present invention include those comprising a sulfated transition metal oxide such as sulfated zirconia together with an oxide of iron or oxides of iron and manganese as described in U.S. patent application Ser. No. 09/296,852, filed Apr. 22, 1999 (Attoney's Docket No. 10144-1), as well as those comprising a mixed oxide of cerium and a Group IVB metal, e.g., zirconium, described in U.S. patent application Ser. No. 09/366,249, filed Aug. 3, 1999 (Attorney's Docket No. 10173-1.)

The process of the invention can also use a solid acid catalyst comprising an oxide of a Group IVB metal modified with an oxyanion or oxide of a Group VIB metal by calcination of the oxide species at a temperature of at least 400° C., as disclosed in U.S. patent application Ser. No. 09/275,749, filed Mar. 25, 1999 (Attorney Docket No. 10135-1). The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; and in an article by K. Arata and M. Hino in *Proceedings 9th International Congress on Catalysis,* Volume 4, pages 1727–1735 (1988).

The large pore crystalline molecular sieves which can be used in the present invention include those which have pores sufficiently large to physically absorb 2,2,4-trimethylpentane. Representative large pore crystalline molecular sieves include, for example the following zeolites: ZSM-3, ZSM-4, ZSM-12, ZSM-18, ZSM-20, zeolite Beta, zeolite L, mordenite, faujasite, zeolite Y, and the rare earth metal-containing forms of the above. For the purposes of this invention, zeolite Y includes zeolite Y in its as synthesized form, as well as its variant forms including framework dealuminated zeolite, e.g., ultrastable Y (USY) described in U.S. Pat. No. 3,293,192 and LZ-210 described in U.S. Pat. No. 4,503,023, hereby incorporated by reference. The large pore zeolite selected for use in the process of this invention generally can possess an alpha value over a wide range of from less than 1 to over 1000. "Alpha value", or "alpha number", is a measure of zeolite acidic functionality and is more fully described together with details of its measurement in U.S. Pat. No. 4,016,218, J. Catalysis, 6, pp. 278–287 (1966) and J. Catalysis, 61, pp. 390–396 (1980). Zeolites of low acidity (alpha values of less than about 200) can be achieved by a variety of techniques including (a) synthesizing a zeolite with a high silica/alumina ratio, (b) steaming, (c) steaming followed by dealuminization and (d) substituting framework aluminum with other species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures using elevated pressure, e.g., at from about 3500° to about 700° F. with from about 10 to about 200 atmospheres. Specific details of several steaming procedures may be gained from the disclosures of U.S. Pat. Nos. 4,325,994; 4,374,296 and 4,418,235, the contents of which are incorporated by reference herein. Aside from, or in addition to any of the foregoing procedures, the surface acidity of the zeolite can be eliminated or reduced by treatment with bulky reagents as described in U.S. Pat. No. 4,520,221, the contents of which are incorporated by reference herein.

Other large pore crystalline molecular sieves which can be used in the present invention include pillared silicates and/or clays; aluminophosphates, e.g., ALPO-5, VPI-5; silicoaluminophosphates, e.g., SAPO-5, SAPO-37, SAPO-31, SAPO-40, SAPO-41; and other metal aluminophosphates. These are variously described in U.S. Pat. Nos. 4,440,871; 4,554,143; 4,567,029; 4,666,875 and 4,742,033, incorporated herein by reference.

The particular class of macroreticular acid cation exchange resins useful as catalysts in the present invention are characterized by substantial porosity, high surface area and a low surface acid concentration, generally less than about 0.5 milliequivalents of hydrogen ion per square meter surface area. The cation exchange resin can contain a small amount of water, generally between 0.5 and 20 percent by weight. The macroreticular resins utilized in the process of this invention are characterized by the presence of acid functional groups and a structure having a high degree of true porosity while possessing rigidity and being subject to minimum volume change when immersed or removed from solvents or solutions.

The macroreticular acid ion exchange resin used is typified by the presence of sulfonic acid groups, e.g., the sulfonated styrene-divinylbenzene copolymer exchange resins such as those commercially available as Amberlyst-15, Amberlyst XN-1005, Amberlyst XN-1010, Amberlyst XN-1011, Amberlyst XN-1008 and Amberlite 200.

Perfluorinated ion-exchange polymers, or porous microcomposites comprising perfluorinated ion-exchange polymer containing sulfonic acid and/or carboxylic acid groups dispersed within a network of a metal oxide such as silica, e.g. Nafion®, are also useful as catalysts in the present invention.

The solid catalyst can be shaped into a wide variety of particle sizes. The particles can be in the form of a powder, a granule, or a molded product, such as an extrudate. In cases where the catalyst is molded, such as by extrusion, the catalyst can be extruded before drying, or partially dried and then extruded. The present catalyst may be extruded by itself, or it may be composited with a matrix material to form the finished form of the catalyst and for this purpose conventional matrix materials such as alumina, silica-alumina and silica are suitable with preference given to silica as a non-acidic binder. Other binder materials may be used, for example, titania, zirconia and other metal oxides or clays. The active catalyst may be composited with the matrix in amounts from 80:20 to 20:80 by weight, e.g., from 80:20 to 50:50 active catalyst:matrix. Compositing may be done by conventional means including mulling the materials together followed by extrusion or pelletizing into the desired finished catalyst particles.

The cleavage reaction of the invention is effected by contacting the cumene hydroperoxide with the solid oxide catalyst described above in the liquid phase at a temperature of 20 to 150° C., preferably 40 to 120° C., and a pressure of −10 to 1000 psig, preferably atmospheric to 400 psig. To effect the contacting of the cumene hydroperoxide, the catalyst may be contained in a stationary bed, and the contacting operation takes place continuously.

The liquid hourly space velocity (LHSV) based on cumene hydroperoxide is within the range of 0.1 to 100 hr$^{-1}$, preferably 1 to 50 hr$^{-1}$. The cumene hydroperoxide is preferably diluted in an organic solvent inert to the cleavage reaction, such as benzene, toluene, cumene and most preferably acetone. Control of the dilution level can be achieved by setting the reflux rate through the tower, or directly adding the recycled overhead containing the solvent to the cumene hydroperoxide feed. The use of a solvent is preferred so as to assist in dissipating the heat of reaction (about 60 kcal/mol).

The packing which may be used in the distillation column employed in the present invention is selected as a function of the efficiency necessary for the distillation operation. The packing can be selected from packings which are well known to the skilled person, such as solids in the form of rings, poly-lobed extrudates or saddle packing. Non-limiting examples of packing are Raschig rings, Pall rings, Intos rings, Berl saddle packing, Novalox saddle packing and Intalox saddle packing. The packing can also be selected from structured packings, for example, FLEXIPAC (registered trademark) sold by Koch, or SULZER CHEMTECH or SULZER (registered trademarks) sold by Sulzer.

A distributing tray which may be used in the process of the present invention is a simple tray which allows the upward passage of vapor and collection then overflow of liquid, as in any distributing tray which is known to the skilled person, in particular if the major portion of the distillation zone to which it belongs is composed of packing. When a distillation tray is used in accordance with the present invention, the tray can be selected from distillation trays which are known to the skilled person, in particular perforated trays, bubble cap trays, or valve trays.

The operation of a catalytic distillation column according to the present invention leads to a distribution of components throughout the column and catalyst bed. The concentration of various components may affect the optimal performance of the catalyst by retarding desired reactions and promoting undesired ones. To achieve optimal operation of the catalyst bed, the bed can be located at a position within the column where the component concentrations are optimal. This may lead to the presence of a separate distillation section acting as a stripper positioned below the catalyst bed.

The invention will now be more particularly described with reference to the following Examples.

EXAMPLE 1

In the process configuration of FIG. 1, phenol and acetone are produced from cumene hydroperoxide in a reactive distillation column 100. A cumene hydroperoxide-containing feed line 110 containing about 80 wt. % CHP introduces feed through inlet 120 at a point above catalyst bed 130 where it is mixed with a diluting portion of acetone derived from column overhead to provide a dilute cumene hydroperoxide mixture which passes through the catalyst bed 130 under cumene hydroperoxide decomposition conditions including a temperature of about 50 to 90° C., a pressure of 0 to 10 psig, and an LHSV of 0.3 to 5 hr$^{-1}$ to provide a product comprising phenol and acetone. The catalyst bed is an unstructured packed bed of solid catalyst. The catalyst is in the form of pellets, typically greater than 1/24" diameter, such that the catalyst bed void volume allows for liquid flow down the bed, and vapor flow up the bed.

The catalyst is prepared as follows: five hundred parts of $ZrOCl_2.8H_2O$ are dissolved with stirring in 3.0 liters of distilled water. To this solution is added 7.6 parts of $FeSO_4.7H_2O$. Another solution containing 260 parts of concentrated $NH_4OH$, 54 parts of $(NH_4)_6H_2W_{12}O_{40}.xH_2O$ and 2940 parts of distilled water was prepared. Both solutions were heated to 60° C. and the heated solutions were combined at a rate of 50 parts/min using nozzle mixing. The pH of the final composite was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. The dried product was calcined to 800° C. in flowing air for 3 hours, and then formed into pellets. The catalyst pellets were thereafter added to the catalyst bed.

Phenol and other heavies formed pass downwardly through the catalyst bed and are withdrawn from the reactive distillation column through lower outlet 140 and are sent for recovery in the distillation section of the plant (not shown). Overheads containing acetone pass upwardly through the column and through upper outlet 150 and thence to a heat exchanger such as condenser 160 and thereafter to overheads receiver 170. The acetone-containing overhead can be withdrawn from the receiver through line 180 or recycled as reflux to an upper portion of the distillation column 190. Dilution of cumene hydroperoxide feed with acetone is controlled by varying the amount of acetone recycled to the distillation column, i.e., setting the reflux rate through the tower. The compositions of the proposed feed and estimated product compositions are provided below in TABLE 2.

TABLE 2

|  | Feed | Overhead Product | Bottoms Product |
| --- | --- | --- | --- |
| Acetone | 0.00 | 99.57 | 8.43 |
| Mesityl Oxide | 0.00 | 0.00 | 0.00 |
| Cumene | 7.70 | 0.00 | 10.26 |
| Phenol | 0.17 | 0.00 | 67.67 |
| α-Methyl Styrene | 0.27 | 0.00 | 9.47 |
| Acetophenone | 2.19 | 0.00 | 2.92 |
| 2-Phenyl-2-Propanol | 7.87 | 0.00 | 0.00 |
| Cumene Hydroperoxide | 81.80 | 0.00 | 0.00 |
| Water | 0.00 | 0.43 | 1.25 |

EXAMPLE 2

Figure 2:
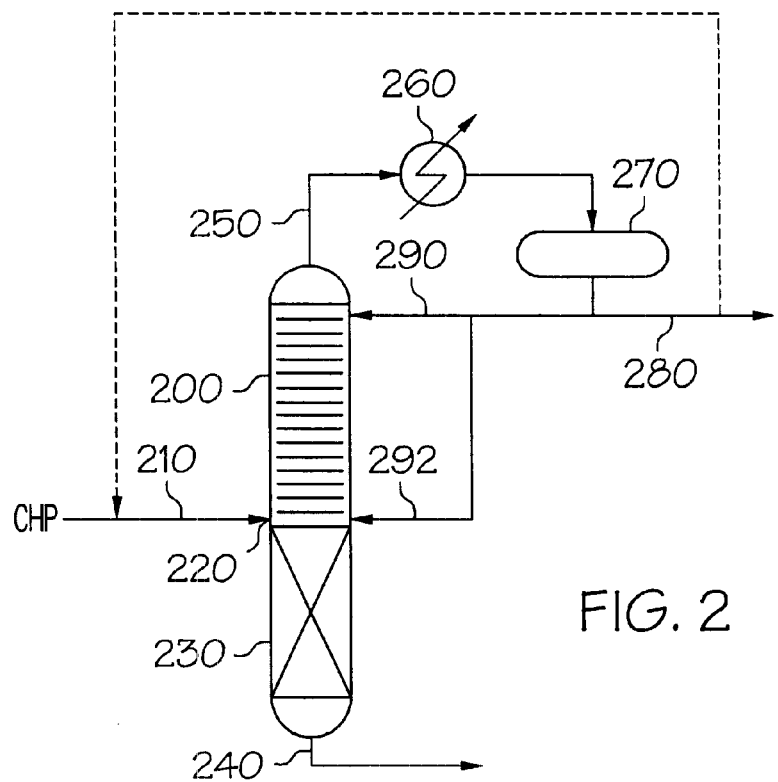
FIG. 2 depicts a flow diagram for an embodiment of the present invention wherein acetone is introduced at the top of the distillation column, directly above the catalyst bed, and/or recycled into the cumene hydroperoxide feed.

In the process configuration of FIG. 2, phenol and acetone are produced from cumene hydroperoxide in a reactive distillation column 200. A cumene hydroperoxide-containing feed line 210 containing about 80 wt. % CHP introduces feed through inlet 220 at a point above catalyst bed 230 where it is mixed with a diluting portion of acetone derived from column overhead to provide a dilute cumene hydroperoxide mixture which passes through the catalyst bed 230 under cumene hydroperoxide decomposition conditions including a temperature of about 50 to 90° C., a pressure of 0 to 10 psig, and an LHSV of 0.3 to 5 hr$^{-1}$ to provide a product comprising phenol and acetone. The catalyst bed is an unstructured packed bed of solid catalyst as described in Example 1. Phenol and other heavies formed pass downwardly through the catalyst bed and are withdrawn from the reactive distillation column through lower outlet 240 and are sent for recovery in the distillation section of the plant (not shown). Overheads containing acetone pass upwardly through the column and through upper outlet 250 and thence to a heat exchanger such as condenser 260 and thereafter to overheads receiver 270. The acetone-containing overhead can be withdrawn from the receiver through line 280 or recycled as reflux to an upper portion of the distillation column through line 290 or through line 292 to a lower portion of the distillation column (at the CHP feed tray level). Alternatively, or in addition, the recycled overhead is directed through line 294 to the cumene hydroperoxide feed 210 as a way to effect dilution as required. Thus, dilution of cumene hydroperoxide feed with acetone is controlled by varying the amount of acetone recycled to the distillation column, i.e., setting the reflux rate through the tower, at upper and/or lower portions of the distillation column, or added directly to the CHP feed. The compositions of the proposed feed and estimated product compositions are provided below in TABLE 3.

TABLE 3

|  | Feed | Overhead Product | Bottoms Product |
|---|---|---|---|
| Acetone | 0.00 | 99.68 | 27.61 |
| Mesityl Oxide | 0.00 | 0.00 | 0.00 |
| Cumene | 7.70 | 0.00 | 8.11 |
| Phenol | 0.17 | 0.00 | 53.42 |
| α-Methyl Styrene | 0.27 | 0.00 | 7.47 |
| Acetophenone | 2.19 | 0.00 | 2.31 |
| 2-Phenyl-2-Propanol | 7.87 | 0.00 | 0.00 |
| Cumene Hydroperoxide | 81.80 | 0.00 | 0.00 |
| Water | 0.00 | 0.32 | 1.08 |

EXAMPLE 3

Figure 3:
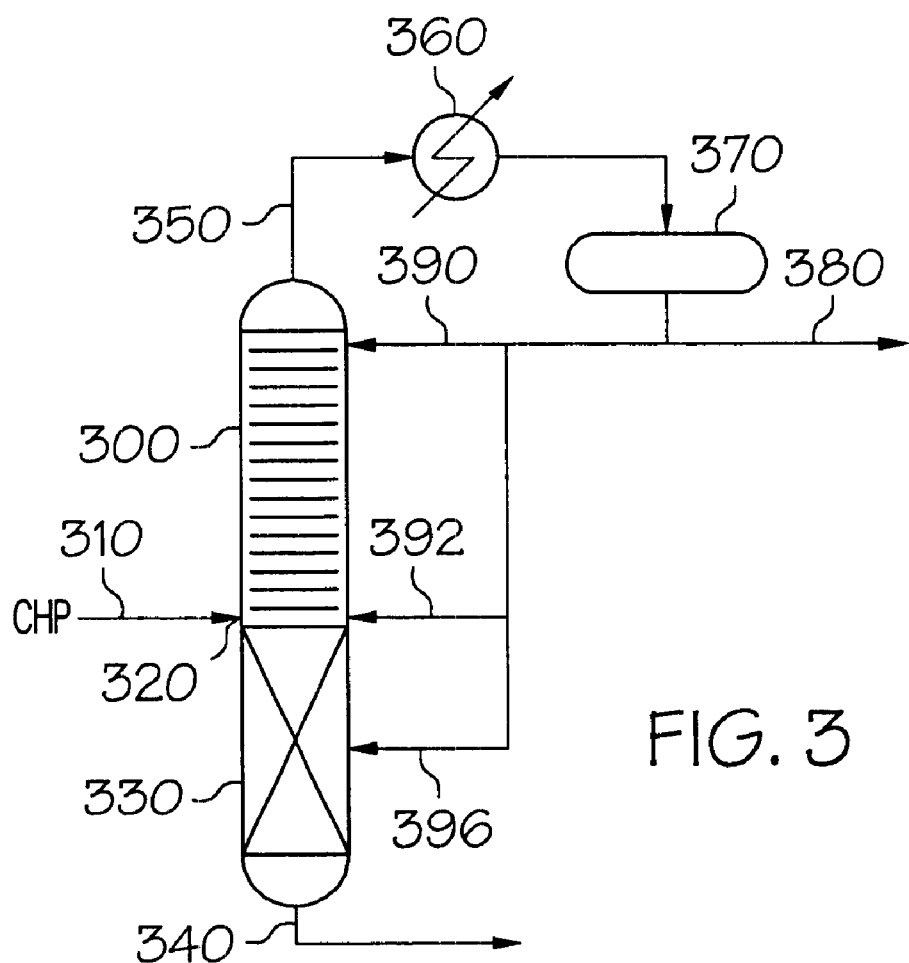
FIG. 3 depicts a flow diagram for an embodiment of the present invention wherein acetone is introduced at the top of the distillation column, directly above the catalyst bed, and/or into the catalyst bed.

In the process configuration of FIG. 3, phenol and acetone are produced from cumene hydroperoxide in a reactive distillation column 300. A cumene hydroperoxide-containing feed line 310 containing about 80 wt. % CHP introduces feed through inlet 320 at a point above catalyst bed 330 where it is mixed with a diluting portion of acetone derived from column overhead to provide a dilute 3 wt. % cumene hydroperoxide mixture which passes through the catalyst bed 330 under cumene hydroperoxide decomposition conditions including a temperature of about 50 to 90° C., a pressure of 0 to 10 psig, and an LHSV of 0.3 to 5 hr$^{-1}$ to provide a product comprising phenol and acetone. The catalyst bed is an unstructured packed bed of solid catalyst as described in Example 1. Phenol and other heavies formed pass downwardly through the catalyst bed and are withdrawn from the reactive distillation column through lower outlet 340 and are sent for recovery in the distillation section of the plant (not shown). Overheads containing acetone pass upwardly through the column and through upper outlet 350 and thence to a heat exchanger such as condenser 360 and thereafter to overheads receiver 370. The acetone-containing overhead can be withdrawn from the receiver through line 380 or recycled as reflux to an upper portion of the distillation column through line 390 or through line 392 to a lower portion of the distillation column (at the CHP feed tray level). Alternatively, or in addition, the recycled overhead can be directed through line 396 directly to the catalyst bed 340. This interstage injection of the acetone-containing overhead may be used to control concentration levels in the lower portion of the catalyst bed to minimize formation of heavy compounds. Thus, dilution of cumene hydroperoxide feed with acetone is controlled by varying the amount of acetone recycled to the distillation column, i.e., setting the reflux rate through the tower, at upper and/or lower portions of the distillation column, or added directly to the catalyst bed. The compositions of the proposed feed and estimated product compositions are provided below in TABLE 4.

TABLE 4

|  | Feed | Overhead Product | Bottoms Product |
|---|---|---|---|
| Acetone | 0.00 | 99.63 | 19.14 |
| Mesityl Oxide | 0.00 | 0.00 | 0.00 |
| Cumene | 7.70 | 0.00 | 9.06 |
| Phenol | 0.17 | 0.00 | 59.71 |
| α-Methyl Styrene | 0.27 | 0.00 | 8.35 |
| Acetophenone | 2.19 | 0.00 | 2.58 |
| 2-Phenyl-2-Propanol | 7.87 | 0.00 | 0.00 |
| Cumene Hydroperoxide | 81.80 | 0.00 | 0.00 |
| Water | 0.00 | 0.37 | 1.16 |

What is claimed is:

1. An apparatus for preparing phenol from cumene hydroperoxide which comprises
   a) a reactive distillation column comprising at its upper portion a distillation column and its lower portion a catalyst bed;
   b) a lower outlet downstream of the catalyst bed for removing high boiling bottom products comprising phenol;
   c) an inlet at or near the bottom of said distillation column for introducing cumene hydroperoxide feed at a point upstream of said catalyst bed;
   d) an upper outlet for removing low boiling overhead products comprising acetone;
   e) a heat exchanger for cooling said overhead products;
   f) an overhead products receiver for receiving cooled overhead products from said heat exchanger, having an outlet from which said overhead products are collected and/or returned to said distillation column; and
   g) overhead products inlet at an upper portion of said distillation column for introducing overhead products reflux from said receiver.

2. The apparatus of claim 1 which further comprises an element selected from the group consisting of
   h) an overhead products inlet at a lower portion of said distillation column for introducing overhead products from said receiver to said distillation column at or near said inlet for introducing cumene hydroperoxide;
   i) an overhead products line which recycles overhead products to the cumene hydroperoxide feed upstream of said inlet for introducing cumene hydroperoxide; and
   j) an overhead products line which recycles overhead products to one or more portions of the catalyst bead.

3. The apparatus of claim 1 which further comprises an overhead products inlet at a lower portion of said distillation column for introducing overhead products from said receiver to said distillation column at or near said inlet for introducing cumene hydroperoxide.

4. The apparatus of claim 1 which further comprises an overhead products line which recycles overhead products to the cumene hydroperoxide feed upstream of said inlet for introducing cumene hydroperoxide.

5. The apparatus of claim 1 which further comprises an overhead products line which recycles overhead products to one or more portions of the catalyst bed.

6. The apparatus of claim 1 which further comprises a stripping section located beneath said catalyst bed.

* * * * *